United States Patent [19]

Baldone

[11] Patent Number: 4,935,448

[45] Date of Patent: * Jun. 19, 1990

[54] TREATMENT OF DISEASES CAUSED BY HERPES VIRUSES

[76] Inventor: Joseph A. Baldone, 1211 Royal St., New Orleans, La. 70116

[*] Notice: The portion of the term of this patent subsequent to Jul. 26, 2005 has been disclaimed.

[21] Appl. No.: 195,152

[22] Filed: May 18, 1988

Related U.S. Application Data

[63] Continuation of Ser. No. 81,546, Aug. 4, 1987, Pat. No. 4,760,079, which is a continuation of Ser. No. 743,889, Jun. 12, 1985, abandoned, which is a continuation of Ser. No. 631,645, Jul. 16, 1984, abandoned, which is a continuation-in-part of Ser. No. 456,732, Jan. 10, 1983, abandoned.

[51] Int. Cl.$^5$ .............................................. A61K 31/14
[52] U.S. Cl. .................................................. 514/642
[58] Field of Search ........................................ 514/642

[56] References Cited

U.S. PATENT DOCUMENTS

| 2,295,504 | 9/1942 | Shelton | 514/642 |
| 2,666,009 | 1/1954 | Stayner | 514/642 |
| 4,262,007 | 4/1981 | Sherrill | 514/643 |

OTHER PUBLICATIONS

Physiciant's Desk Reference, 6 ed., p. 491, (1952).

*Primary Examiner*—Jerome D. Goldberg
*Attorney, Agent, or Firm*—Finnegan, Henderson, Farabow, Garrett & Dunner

[57] ABSTRACT

This invention pertains to a method of treating diseases caused by Herpes Simplex Virus (HSV) Types 1 and 2. Disclosed herein is a method of treatment that, through the use of Tetraethylammonium Ion (TEA) achieves a selective and specific inhibition of viral function in diseases causes by HSV Types 1 and 2. TEA can be provided in the form of its chloride salt, unpreserved for individual doses, or with preservatives for multiple dose vials.

12 Claims, No Drawings

TREATMENT OF DISEASES CAUSED BY HERPES VIRUSES

This is a continuation of application Ser. No. 081,546, filed Aug. 4, 1987, now U.S. Pat. No. 4,760,079, which is a continuation of Ser. No. 743,889, filed June 12, 1985, now abandoned, which is a continuation of Ser. No. 631,645, filed July 16, 1984, now abandoned, and which is a continuation-in-part of Ser. No. 456,732, filed Jan. 10, 1983, now abandoned.

BACKGROUND OF THE INVENTION

1. Field of Invention

The present invention relates to a method of treating diseases caused by Herpes Simplex Virus (hereafter referred to as HSV) Types 1 and 2. More specifically, the invention relates to the parenteral, topical and/or oral administration of the tetraethylammonium ion (hereafter sometimes referred to as TEA) either before or after the HSV has infected the host.

2. Prior Art and General Background

There are two main strains of Herpes Simplex Virus (HSV), Types 1 and 2. Although they are capable of strong cross reaction in some assays, they can be differentiated by neutralization kinetics and, with greater accuracy, by restriction analysis of their purified deoxyribonucleic acid (DNA). Generally, infection by HSV Type 1 is associated with oral, facial and ocular lesions; infection by HSV Type 2 with genital and anal lesions.

Both HSV Types 1 and 2 show a predilection for ectodermal tissues such as in their production of lesions in skin, oral cavity, vagina, conjunctiva and the nervous system. HSV Type 2, which is usually transmitted venereally, is now epidemic in the U.S.A. Some twenty million persons are presently afflicted with this disease in this country. New cases and recurrences exceed 500,000 annually. HSV infections often cause blindness, neonatal deaths, encephalitis, etc. and additionally results in huge economic losses to the nation and the world.

(i) Pathogenesis of HSV Disease

An important characteristic of these viruses is their ability to persist in a latent, or quiescent, form in man and animals.

Initial or primary infections by HSV Types 1 and 2 are contracted through breaks in the mucus membrane where they replicate locally. From there they spread to the regional lymph nodes and, occasionally, they can invade the bloodstream, producing viremia.

When the primary infection subsides or recedes, the virus persists in a latent form in the sensory ganglia which innervate the site of primary infection. In ocular or oral infections, the viruses persist in the trigeminal ganglia. In genital infections, the viruses persist in the sacral ganglia.

Although the state of the viral genome during latency is not yet known, latency can be upset, resulting in viral multiplication. This produces the second form of the disease, which is the recurrent form. Recurrences usually occur at the primary sites. Such recurrent disease in humans can be induced by heat, cold, sunlight (ultraviolet light), hormonal and emotional disturbances, or by immunosuppressive agents.

The natural source and host for HSV Types 1 and 2 disease is man and the primary mode of transmission is by close personal contact.

(ii) Epidemiology of HSV Diseases

Epidemiological control of HSV is poor because the majority of the population, up to 90%, has been exposed to the viruses. In the healthy carrier the viruses can be isolated in the tears, saliva, vaginal and other secretions, even during the absence of overt disease.

Past treatments of the disease have been largely ineffective. To successfully stop the growth of a virus, an agent must selectively inhibit any of the viral specific functions such as (1) adsorption, (2) uncoating, (3) transcription, (4) protein synthesis, (5) nucleic acid replication, (6) maturation, and (7) release.

Among agents thus far used to treat HSV are: Idoxuridine (IDU), Cystosine Arabinoside (ARA-C), Adenine Arabinoside (ARA-A), Trifluorothymidine (TFT), and Acyclovir. Interferon has also been used for HSV treatment. All of these therapies interfere with viral and host cellular functions. Because of host cell toxicity these compounds have been largely ineffective for systemic use in humans.

Until this invention there has been no drug shown to be capable of selective inhibition of viral function. The inventor has demonstrated that TEA in the manner utilized does selectively inhibit viral function. The antiviral properties of TEA toward HSV Types 1 and 2 is shown by the results in the detailed description of the invention given below. Similar properties are expected of the homologues of TEA.

It is therefore an object of the present invention to provide an effective method of treating HSV Types 1 and 2.

The present invention is directed to the use of TEA ion to treat HSV Types 1 and 2. The TEA ion has the following structure:

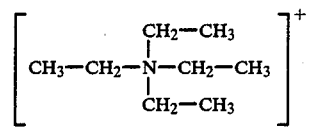

TEA chloride is listed in the *American Druggist's Blue Book* (1974) Am. ed. as being sold by: City Chemical Corp., 132 W. 22nd Street, New York, NY 10011.

Description of a process for manufacture of TEA is given in U.S. Pat. No. 2,653,156 Sept. 22, 1953 by Deutsch, et al. which also notes generally the disinfectant properties of quaternary ammonium compounds of which TEA chloride is one.

Similarly, U.S. Pat. No. 4,165,375 issued Aug. 21, 1979 to Berger et al. contemplates the general use of quaternary ammonium compounds in a low foaming medium for external use as a general disinfecting agent.

U.S. Pat. No. 2,689,814, issued Sept. 21, 1954 to Nicholls et al. similarly noted the germicidal effectiveness of TEA as well fungicidal and anesthetic properties of quaternary ammonium compounds. U.S. Pat. No. 2,886,487 issued on May 12, 1959 to Kupferberg et al. also describes the use of such quaternary ammonium compounds in topical application.

In the 1949 edition of the *Physicians' Desk Reference*, the product "Etamon Chloride," was reported to contain 0.1 g of tetraethylammonium chloride in each cc. and described, to-wit; "reversibly blocks transmission of the motor impulses of both the sympathetic and parasympathetic divisions of the autonomic nervous system. In conditions associated with vasospasm it causes vasodilation. Used in herpes zoster, postherpetic pain, causalgia, thromboangiitis obliterans (Buerger's disease), Raynaud's disease, thrombophlebitis, trenchfoot, and immersion foot." In the 1954 edition of *Physicians' Desk Reference* any claim with respect to herpes zoster was omitted. In the 1960 edition of the *Physicians' Desk Reference* the product was no longer listed, and subsequently the manufacture of the product in pharmaceutical purity was discontinued. It is further noted that this product contained as a preservative benzethonium chloride, which preservative, in accordance with U.S. Pat. No. 4,262,007 to Sherrill (issued Apr. 14, 1981), is effective in treating herpes zoster, etc.

In *The Pharmacological Basis of Therapeutics* (2nd Ed.) by Goodman and Gilman (1955; MacMillan) in a discussion of the therapeutic uses of TEA, TEA's role as a pain reliever was mentioned in relation to, inter alia, herpes zoster as follows: "In various types of causalgia and related painful posttraumatic states, herpes zoster, and chest pain caused by embolism, neoplasm, pleuritis, etc., TEA is of value in relieving pain, in a few instances permanently, and may be a useful diagnostic tool for selecting cases which might be relieved by sympathectomy".

Additional prior patents which may be of interest are listed below:

| Patent No. | Patentee(s) | Issue Date |
| --- | --- | --- |
| 2,295,504 | Shelton | Sept. 8, 1942 |
| 2,666,009 | Stayner | Jan. 12, 1954 |

GENERAL DISCUSSION OF THE INVENTION

The present invention contemplates an improved method for the treatment of diseases in a mammal caused by HSV Types 1 and 2. The treatment involves administering the tetraethylammonium ion, usually as TEA chloride, to the infected host.

TEA acts as a ganglionic blocking drug reversibly blocking both sympathetic and parasympathetic motor impulses.

Secondary effects include the lowering of blood pressure due to pronounced vasodilator action, mydriasis (pupil dilation), cycloplegia (which may cause temporary blurred vision), ptosis (eye-lid drooping) and similar impairment of physical responses associated with its nerve impulse blocking action.

Treatment of diseases caused by HSV Types 1 and 2 with TEA has not been advocated prior to this invention.

Dosages parenterally, that is for example intravenously and intramuscularly, vary when using TEA. The intravenous dose in adult humans is 200 to 500 milligrams (not to exceed 7 mg per Kg of body weight). The intramuscular dose in adult humans is 1000 to 1200 milligrams (not to exceed 20 mg per Kg of body weight). The LD-50 in rats is 2,630 milligrams per kilogram of body weight.

The action of TEA does not modify conduction of nerve impulses but only blocks transmission of these impulses. This blocking action is fully reversible and treatment of excessive dosages is known in the art, such as the administration of acetylcholine.

Lesions caused by HSV Types 1 and 2 are manageable and self-limiting in most cases, but in many cases recurrences cause severe problems, for example, blindness through scarring of the cornea, encephalatis, neonatal deaths, etc.

It is known and accepted that the latent viruses reside in the ganglia and are reactivated to produce recurrent episodes of the disease. Inductions of recurrent episodes of the disease have been experimentally produced in animals by a variety of stimuli including physical manipulation of the sensory ganglia. In all cases of reactivation a change is seen in the reservoirs, the ganglia. It is therefore concluded that an agent which achieves host ganglionic blockage may have a profound effect on the recurrent diseases caused by HSV Types 1 and 2.

In individual doses it is advocated that unpreserved TEA be used. For multiple dose vials, preservatives may be used. Exemplary preservatives are benzyl alcohol, butylparaben, chlorobutanol, metracresol, methylparaben, myristylgamma picolinium chloride, phenol, phenylmercuric nitrate, propylparaben and thimerosal.

Elsewhere in this disclosure is described in detail the antiviral activity of TEA. It is shown that it inhibits the in vitro replication of HSV Types 1 and 2. This antiviral activity was achieved when the compound was added before or after viral inoculation. Changes in cell morphology at high concentrations were totally reversible. It was also demonstrated that the activity of TEA did not impair cell metabolic processes. These discoveries indicate that this compound may be utilized as a selective and specific inhibitor of viral growth.

Additional objects and advantages of the present invention and treatment is presented in the detailed description which follows.

DETAILED DESCRIPTION OF THE PREFERRED EMBODIMENTS

The preferred embodiments of the invention include:
(i) the parenteral, topical, oral and/or vaginal administration of the tetraethylammonium (TEA) ion to persons infected with HSV Types 1 and/or 2 (whether or not the virus is symptomatically manifest) for the purpose of, inter alia:
  (a) the amelioration and/or elimination of any of the symptoms of HSV Types 1 and/or 2;
  (b) the prevention and/or amelioration of any recurrence(s); and/or
  (c) the prevention and/or amelioration of viral shedding.; and
(ii) the prophylactic administration of the TEA ion to persons who risk exposure to infection by HSV Types 1 and/or 2. This would usually, but not necessarily, involve a topical or vaginal administration.

For parental administration the TEA ion (most preferably as tetraethylammonium chloride which has proven to be safe) is dissolved in a pharmaceutically acceptable diluent or carrier including but not limited to normal sterile saline. The concentration of TEA (measured as its chloride) is limited only by the amount which may be carried or dissolved in a pharmaceutically acceptable carrier or diluent, but preferably is administered in a concentration range from about 1 to about 1000 mg per ml (total volume), more preferably in a range of from about 50 to about 250 mg/ml and is typically administered at a concentration of approximately 100 mg per ml (total volume). For topical and/or vaginal administration the TEA ion (again most preferably as tetraethylammonium chloride) is dissolved in a pharmaceutically acceptable diluent or carrier, including but not limited to hydrophilic ointment bases. The concentration of TEA (measured as its chloride) may range, without limitation, from, 0.01 percent to 50 percent (total volume). By employing the technique of micro-encapsulation, it is anticipated that TEA ion, preferably as tetraethylammonium chloride, will be able to be administered by oral dosage with a sufficiently controlled delivery.

IN VITRO EXPERIMENTS

In order to test the effectiveness of treating diseases caused by HSV with the TEA ion, in vitro tests were performed and verified by two additional duplicate experiments for reproducibility. The test safeguards, procedures and results given below show the effectiveness of the invention.

The overall aim of the experiments was to determine the antiviral properties of the TEA ion, in particular tetraethylammonium chloride, (hereafter referred to as TEA Cl). Specifically the determination of whether compound TEA Cl inhibit the in vitro replication of Herpes Simplex Virus 1 and 2, hereinafter referred to as HSV-1 and HSV-2, was sought.

METHODS AND MATERIALS (1) Cells and Viruses

Monolayer cultures of Vero, RK-13 (rabbit kidney) and WISH (human amnion, Hayflick) cells were used in the study.

The cells were grown in Basal Minimal Eagle's Media supplemented with 5% fetal calf serum, 1% glutamine, sodium bicarbonate and antibiotics. Cultures were maintained with the same media containing 2% fetal calf serum (maintenance media).

The F strain of HSV-1 was chosen because it is a well known prototype of HSV-1. It can be obtained from the American Type Culture Collection, 12301 Parklawn Drive, Rockville, Md. 20852. It is identified as ATCC-VR 733. For studies with Type 2, the G strain (ATCC-VR 734) and also the 333 strain were used.

(2) Plaque Inhibition Assays effectiveness in the suppression of viral growth. The drug was added after adsorption of the virus in one set of experiments (Pre-inoculation experiments—see below); and prior to infection of the cell cultures in others (Pre-incubation experiments — see below).

In one instance, the effect of the drug on a cell that has already been infected with the virus having already penetrated into the cell's cytoplasm, was being measured. In the other experiment, the cell cultures were treated with the drug prior to the inoculation to determine if these cells then would be permissive or non-permissive to this virus. Plaque reduction assays give a quantitative measure of anti-viral activity and is reliable and objective.

2(a) Pre-Inoculation Experiments (Assays)

Monolayer cultures of WISH cells were grown in 25 cm$^2$. Plastic bottles or 6 well cluster dishes and were inoculated with 0.2 ml of the virus strain. The virus was allowed to adsorb for 45 minutes at 37° C. with gentle rocking of the cultures every 15 minutes. After the adsorption period, 1 ml of the drug dilution plus maintenance media were added to the cultures. The 25 cm$^2$. flasks received 1 ml of the drug dilutions plus 4 mls of maintenance media per well (6 33 mm diameter wells per cluster dish). Cluster dishes received 1 ml of drug dilution plus 3 mls of media. All cultures were prepared in duplicate.

2(b) Pre-incubation Experiments (Assays)

In these experiments, the media was either decanted or gently aspirated from the cultures; then 1 ml of drug dilution plus 1 ml of maintenance media was added. The cultures serving as virus controls or cell controls received 2 mls of maintenance media. After the pre-treatment period the, media was again aspirated, and the cell cultures were infected as described above.

The cultures were incubated at 37 degrees C. for 36–48 hours or until the virus control showed discrete visible plaques. When this occurred the cultures were fixed and stained with crystal violet, and the plaques counted under the microscope for precision. An average plaque count was obtained for both the treated & control cultures and the averages then compared. By this comparison, percentages of plaque inhibition in the treated cultures were then calculated.

(3) Toxicity

For the toxicity experiments, all 3 cell lines—RK-13, Vero cells, and WISH cells were used. In these experiments, the effect of the drug on the uninfected cell for a range of periods of time was determined. Accordingly, cultures were incubated with and without the drug. The time of exposure was from one to seven hours. A comparison was then made between the TEA Cl treated cultures and the control cultures.

After each period of incubation, the cells were washed, and fresh media was put in. The cell viability was then determined by dividing these cultures and having them grow into two new cell cultures.

(4) Drug Dilution

All drug dilutions were made in maintenance media.

RESULTS (1) Toxicity

Experiment #1

The effect of TEA on monolayer cultures of Vero and WISH cells was determined. Confluent monolayer cultures of 25 cm$^2$. plastic bottles were incubated overnight at concentrations of 5, 2.5 and 1.25 mg of TEA Cl per culture. No change in morphology of the cells was seen. At the end of the incubation period, the cultures were washed twice with sterile PBS (Dulbecco). Fresh medium was added to each of the cultures which were then incubated for an additional 24 hours. There was no apparent difference in the growth or general appearance between the treated cultures and the untreated controls.

Although there was no detectable difference between Vero and WISH, the latter, the human cell line, was chosen for use.

(2) Anti-viral activity

Experiment #2

Confluent monolayer cultures of Vero cells were infected with the F strain of HSV-1. After the adsorption period, the cultures received 1 ml of TEA Cl at a concentration of 2.5 mg/ml plus 4 mls of maintenance media. Control cultures received no drug. Cultures were stained at the appropriate time and the plaques were counted. Drug-treated cultures had an average of 75.5 plaques and the control cultures had an average of 488.5 plaques. The rate of plaque inhibition was therefore 84%. In addition, the size of the plaques in the treated cell cultures were appreciably smaller than those present in the control cultures.

Experiment #3

Based on the results obtained in the preceeding experiment, definition of the antiviral activity of TEA Cl in WISH cells was determined. The dilutions of TEA Cl were 10, 5, 2.5 and 0.65 mg/ml. The HSV-1 (F) strain of virus was used. After adsorption for 45 minutes, one ml of drug dilution plus 3 mls of media was placed into each of two wells.

In another plate, duplicate wells received 1 ml of drug dilution plus 1 ml of media and were incubated for 3 hours. Then the media was aspirated, the cultures infected, and fresh media was added. They were incubated at 37 C. until discrete plaques were observed in the control wells.

The findings from this experiment (Table I) are as follows:

(1) Antiviral activity was seen in all the dilutions tested.

(2) Where the drug was added after inoculation with the virus, there was no strict correlation between viral inhibition and dosage; for example, drug concentrations of 5 and 2.5 mg/ml which differ by a factor of 2 gave similar degrees of inhibition, namely, and 46 percent, respectively.

(3) Pre-incubation of the cell monolayer with mg/ml of the drug, prior to inoculation with the virus inhibited 71% of the plaques. Pre-incubation with and 2.5 mg. gave 22 and 10 percent inhibition which is not considered significant.

TABLE I

Effects of compound TEA Cl in Herpes Simplex Virus Replication
HSV-1 (F)

| mg/cultures | % plaque inhibition |
|---|---|
| drug added after inoculation with the virus | |
| 10 | 56 |
| 5 | 45 |
| 2.5 | 46 |
| 1.25 | 39 |
| .62 | 30 |
| 3 hours pre-incubation | |
| 10 | 71 |
| 5 | 22 |
| 2.5 | 10 |

Conclusion from Experiment #3

Pre-incubation of the cells with 10 mg/ml solution of the drug rendered the cells non-permissive to the virus (71% plaque inhibition).

Where the drug was added after inoculation with the virus, significantly different drug dilutions (from mg/culture to 0.62 mg/culture) gave similar degrees of plaque inhibition. From this finding it is concluded that the mode of action of TEA is other than by viral metabolic process.

Experiment #4

This experiment uses the same protocol as the preceeding one, except that the drug concentrations were increased by a factor of ten. The data is shown in Table II.

TABLE II

Effect of TEA Cl in Herpes Simplex Virus Replication
HSV-1 (F)

| mg/culture | % plaque inhibition[a] | % plaque inhibition[b] |
|---|---|---|
| 100 | toxic | 79 |
| 50 | 100 (thin) | 82 |
| 25 | 100 (thin) | 79 |
| 12.5 | 62 | 80 |
| 6.2 | 20 | Not Done |

[a]Drug added after virus adsorption
[b]Cultures pre-incubated with the drug 3 hours before infection.

The previous findings were confirmed. Pre-incubation of the cells with several dilutions of the drug gave comparable degrees of plaque inhibition. Those cultures that received the drug prior to inoculation gave relatively the same degree of protection (79–82 percent) regardless of concentration.

In the other cultures in which the drug was added after the adsorption period, the following was found: 100 mg per culture were toxic and the cells have lifted off the plate. The next concentrations, 50 and 25 mg per culture, no plaques formed, but the cell layer was "thin". The word "thin" means that the cells are still attached to the container, but the monolayer is not confluent, and there are spaces between the individual cells.

The 62% plaque-inhibition observed in the cultures containing 12.5 mg is consistent with the 56% plaque inhibition per 10 mg of drug found in the preceeding experiment.

Experiment #5

In this experiment the anti-viral activity of TEA was tested at different concentrations of the drug and at different pre-incubation periods.

WISH cells were pre-incubated with 100, 50, 25, 12.5 and 6.2 mg of TEA Cl per culture for 2, 4 and 7 hours prior to infection with HSV-1(F).

The results of the experiment are set out in Table III below:

TABLE III

Effect of compound TEA Cl on Herpes Simplex Virus Replication HSV-1 (F):

| Pre-incubation time | mg/culture | % plaque inhibition |
|---|---|---|
| 2 hours | 100 | 68 |
| " | 50 | 24 |
| " | 25 | 17 |
| " | 12.5 | 18 |
| " | 6.2 | 0 |
| 4 hours | 100 | 100 (thin) |
| " | 50 | 63 |
| " | 25 | 37.5 |
| " | 12.5 | less than 20 |
| " | 6.25 | less than 20 |
| 7 hours | 100 | 100 (thin) |
| " | 50 | 95.7 |
| " | 25 | 96.5 |
| " | 12.5 | 76 |
| " | 6.25 | 50 |

In these controlled experiments, the TEA anti-viral activity was observed to be dependent on both concentration and duration of exposure to the drug. Example: 50 mg/culture gives plaque-inhibition rates of:
 24% at 2 hours pre-incubation
 63.0% at 4 hours pre-incubation
 95.7% at 7 hours pre-incubation.
Somewhat the same is seen with 25 mg per culture, where (as shown in Table III) the percent inhibition rises from 17% to 96.5% with time.

Experiment #6

The effect of TEA was then tested against Herpes Simplex Virus Type 2.

Table IV shows the results of one experiment. The percent inhibition of 56% with 50 mg/culture pre-incubation time of 2 hours is consistent with the results found with HSV-1. HSV-2 (333) appeared to be more sensitive to the drug. The HSV-2 (G) strain was also tested, giving similar results.

TABLE IV

Effect of compound TEA on Herpes Simplex Virus Replication HSV-2 (333) strain

| Pre-incubation time | mg/culture | % plaque inhibition |
|---|---|---|
| 2 hours | 50 | 56 |
| " | 25 | 42 |
| " | 12.5 | 25 |
| " | 6.25 | 0 |

TOXICITY

The apparent toxicity that was described as "thin", is totally reversible. When the drug is removed and fresh media is added, the cell layer reverts to its normal non-treated appearance.

No change in morphology or cytopathic effect was seen in the cultures containing the drug nor those without the drug. There was no difference in the rate of growth of drug-tested cultures and those without drug. These observations indicate that the drug is not toxic to cells at the concentrations used.

SUMMARY OF IN VITRO RESULTS

1. Compound TEA Cl inhibits the in vitro replication of Herpes Simplex Virus Types 1 and 2.
2. The anti-viral effect of TEA is present whether it is added before or after viral inoculation.
3. When TEA was added before viral inoculation, it rendered the cells non-permissive to the virus and no plaques were formed. In these experiments, the anti-viral activity was time and dosage dependent.
4. Suppression of viral growth was evidenced not only by the reduced size of the plaques but by the number of plaques.
5. These preliminary experiments suggest that the mode of action of TEA is not impairment of the cell metabolic process.
6. The observed toxicity or changes in the cell's morphology was totally reversible.

CLINICAL TESTING

At the present time TEA Cl is not sold in pharmaceutical purity, although its safety for pharmaceutical use is well established. Accordingly, reagent grade TEA Cl was obtained and purified to pharmaceutical grade and administered to patients exhibiting acute symptoms of Herpes Simplex Virus Type 1 and/or 2 to test the efficacy of the drug as a treatment for the diseases caused by the viruses. All parenteral administrations of the drug described hereunder were made by intravenous infusion.

CLINICAL CASE A

Patient A is a 43 year old female who first reported on Oct. 14, 1983 with a history of herpetic lesions on her buttocks which had erupted approximately every 30 days for several years previously (over a 10 year period, with increasing frequency during the past 2 years). She was referred by a Board certified Dermatologist who had diagnosed HSV Type 2 and who had treated the lesions of at least five attacks with steroid injections. The lesions usually lasted from between seven days to six weeks. The patient experienced periodic pain in the buttocks with chronic severe sciatic pain radiating down her right leg.

Patient A appeared for treatment two days following the latest eruption of lesions on her buttocks. She weighed 57 kg. and was administered 2.8 cc. of a solution of 100mg of TEA Cl per cc. of normal saline. (This solution was used in all parenteral administrations described herein). At the time of treatment she experienced some blurred vision and slight dizziness on rising to the seated position. However, immediately following the infusion she reported cessation of sciatic pain.

The patient called approximately three weeks later reporting that she was asymptomatic. She subsequently reported that she had gone 52–53 days without lesions or pain at which time a few vesicles had appeared without weeping or crusting and disappeared in two to three days without pain.

On Dec. 14, 1983 the patient reported that several small lesions had developed on the previous day with mild sciatic pain. She was given a second infusion of 3.2 cc. Immediately after this treatment she experienced some blurred vision but the sciatic nerve pain disappeared during the infusion.

Three days later, the patient had 6 to 8 patches of lesions developing over a larger area with some pain but no vesicles had developed yet. The patient also had pain in the back and down both legs.

Two days later on Dec. 19, 1983 the patient was given a third infusion of 3.4 cc.

Approximately two weeks later, the patient reported a few tiny areas under the skin but without eruptions and the tiny areas disappeared in about a day. About three weeks later there was no further pain or lesions. About three weeks later, the patient continued to be trouble free. About one week, later the patient reported that a few spots came up without aura, and that these were gone in 24 hours.

The patient was last contacted on July 9, 1984 at which time she advised that she has experienced no further lesions or pain.

CLINICAL CASE B

Patient B is a 43 year old male diagnosed as having both HSV Type 1 (expressed as oral lesions) and HSV Type 2 (expressed as penile lesions). He weighed 75 kg when he reported on Oct. 21, 1983 and was administered 3.7 cc of TEA Cl (5 mg/kg). Immediately following infusion, the patient reported blurred vision, dryness of the mouth, and unsteady gait; however, these drug related effects ceased 10–15 min. after cessation of infusion.

In a call to the patient 3 days later he reported that his oral lesions had been resolved, resolution occurring in a shorter than usual time.

About three weeks later, the patient described a labial aura and predicted a massive outbreak. He was administered an additional 3.7 cc on Nov. 11, 1983. The following day the patient reported an absence of an aura and no occurrence of the expected lesion except for a very small lesion at the corner of the mouth which was cultured out as HSV 1. About a month later the patient reported a "chapped lip-like" area but that the attack was never serious and that no lesion appeared.

On Dec. 21, 1983 the patient returned for treatment of acute penile lesions of HSV Type 1 and 2. He was administered 4.5 cc (6.0 kg/mg). Eight days later, the patient reported that the lesion had dried the next day and crusted and disappeared in 2-3 days. The patient reported feeling that his active lesions obviously respond to treatment but that reccurrences are not eliminated.

About three days later, lip lesions appeared, and the patient requested further treatment. He was administered 4.8 cc on Jan. 2, 1984. About 5 days later, the patient reported that a labial and penile lesion were starting. The patient was contacted about two weeks later, and reported that the last treatment appeared of no value. He reported that he had had painful penile lesions that lasted 8 days. About a month later, however, the patient reported that he had no more attacks, which he attributed in part to the treatment.

CLINICAL CASE C

Patient C is a 26 year old male who weighed 77 kg when he reported for treatment on Nov. 4, 1983. He was diagnosed as having multiple Herpes Simplex Virus infection since the age of 6 months. He appeared for treatment with labial lesions and a large lesion in the middle of his back. He also had lesions on his forehead. In the past he had lesions nasally. He had at times experienced remissions of 4-5 months.

The patient was infused with 3.85 cc (5 mg/kg) TEA Cl solution on Nov. 4, 1984 and experienced slightly blurred vision.

The next day, the patient reported that the lesions were markedly improved, especially on his forehead. Three days later, the patient experienced lesions. However, three additional days later it was acknowledged that two attacks of labial lesions cleared rapidly. A week later, the patient reported having only a few fever blisters that cleared right away. The patient reported the same a week later. No problems were reported until about a month later when the patient reported a lesion on the forehead that crusted relatively quickly. The patient was contacted on Feb. 18, 1984 and July 10, 1984 and reported that he had experienced no further problems.

CLINICAL CASE D

Patient D is a 37 year old female who weighed 56 kg when she reported for treatment on Nov. 18, 1983. For the past 5 years, she had experienced lesions on her buttocks, with symptoms worsening prior to her menstrual cycle. There was no time she reported when there was a cessation of lesions or auras.

She was administered 2.8 cc TEA Cl solution (5 mg/kg) on Nov. 18, 1983 and experienced dry mouth and transient blurred vision. Two days later she reported that all lesions were improving and that itching and tingling disappeared with the treatment.

CLINICAL CASE E

Patient E is a 34 year old male who weighed 93 kg when he reported for treatment on Nov. 23, 1983. He had a history of HSV Type 2 penile lesions occurring at least once per month with the lesions sometimes lasting 3 months. He was administered 4.8 cc of TEA Cl (5 mg/kg) on Nov. 23, 1983 and experienced slightly blurred vision. Two days later, he reported that the lesions had started to crust; however, he then experienced a massive prodome with large weeping lesions which were unlike any lesions of the previous 5 years.

The patient returned on Dec. 9, 1983 without lesions but feeling that he was in a "prodrome stage". He was administered another 4.8 cc of TEA Cl solution on that day. The next day he reported no prodome and no lesions, but the following day reported that another breakout was occurring.

On Dec. 15, 1983 the patient was 99% cleared with 2 pinpoint lesions remaining. He was infused with a further 5 cc of TEA Cl on that day. Three days later the patient reported only pinpoint sites and felt that each infusion caused a definite change in the disease. Two days later the patient reported that all lesions had cleared up. On Dec. 24, 1983 vesicles had appeared which quickly disappeared without crusting, and that one new lesion had appeared.

Three days later on Dec. 27, 1983 the patient reported that the final lesion had gone but that "some lesions are trying to come". Two days later the lesions had not come. A week later, the patient reported that prodome started 3 days earlier with 5-6 pinpoint lesions breaking out on the following day on the right dorsal side of his penis.

CLINICAL CASE F

Patient F is a 31 year old male diagnosed as having HSV Type 2 infection of his penis. He reported a history of penile lesions approximately every two months lasting 1-0742 2 weeks. He weighed 75 kg when he reported on Nov. 23, 1983 and was administered 3.8 cc (5 kg/mg) of TEA Cl. The next day the patient considered his lesion improved. The following day the patient's dermatologist found a small lesion. Three weeks later the patient noticed a small new lesion.

On Dec. 20, 1983 the patient reported with a lesion on the base of his penis and was administered 4.5 cc of TEA Cl. Nine days later the patient stated that the lesion had cleared in 48 hrs., but on the other side lesions had developed.

On Dec. 30, 1983 the patient was infused with a further 4.0 cc of TEA Cl. Within 4 days the lesions had cleared up. About 3 weeks later, the patient reported that a new lesion had appeared earlier at the same site, was open for a day or so, and then crusted and that now his general condition was the best it had been for several months and that he was completely cleared up.

On Feb. 9, 1984 the patient reported that he had had one lesion that lasted a week and another that cleared up quickly and that he was in "good shape". The patient subsequently had lesions that lasted 12 days and 7 days.

CLINICAL CASE G

Patient G is a 36 year old male who weighed 78 kg and was diagnosed as having HSV Type 2. He reported that penile lesions had erupted every 2 weeks to 3 months (usually every 1-1 ½ months) for the previous 7 years. Lesions were acute for 2-3 days followed by 4 days of scarring.

When he reported for treatment on Dec. 7, 1983 the patient reported experiencing labilais prodrome without lesions and also a sensation in his lower back. He was administered 4.3 cc of TEA Cl solution on that day. The next day he reported the treatment to be "great" with the lesions improving, and 2 days later he reported the "lesions" were gone with no crusting, skin smooth, visable capillaries disappeared, softer circumcision scar, no back sensation, psoriasis improved, but some reddening of the lip where the patient had never had a lesion. 3 days later he reported everything fine except two pinpoints red spots that the patient did not feel would become vesicles. A week later on Dec. 20, 1983 the patient reported that the lesions had never crusted and were gone within 48 hours.

After over a month with only a minor tingling incident the patient reported with 2 penile lesions on Jan. 24, 1984 and was administered 4.5 cc of TEA Cl solution. He was also infused with a further 4.5 cc of TEA Cl the next day. The patient remained relatively stable for about a month; however, after an additional month with no new infusion, the patient was back to his pre-treatment state.

The patient was contacted on July 10, 1984 at which time he stated that he was at his pre-treatment state.

CLINICAL CASE H

Patient H is a 41 year old male who weighed 77 kg when he reported on Jan. 27, 1984. He was diagnosed as having HSV Type 2. The patient reported that for the last 2 years he had had penile lesions (lasting 7-10 days) approximately every 2 months. A lesion had started the day before he reported. He was treated with 4.6 cc of TEA Cl (6.0 mg/kg) on Jan. 27, 1984. The following day the patient reported striking improvement, but experienced a setback 6 days later when the condition became a visual attack. The attack disappeared.

The patient was contacted on July 11, 1984 at which time he advised that besides 2 minor incidents of red spots (which did not develop) and some aura, he has had no further problems and, in particular, no further vesicles since the attack immediately following his treatment cleared.

CLINICAL CASE I

Patient I is a 42 year old male who weighed 86 kg when he reported for treatment on Feb. 9, 1984. He was diagnosed as having both HSV Types 1 and 2. The patient reported he had had good health until 1977 when he developed herpetic lesions in and around the mouth, chin and cheeks, unexplained nocturnal headaches, penile lesions and symptoms similar to those of stomach ulcers. His stated his lesions were almost constantly present. He was infused with 4.7 cc. of TEA Cl solution on Feb. 9, 1984. The next day, the patient reported a sore had started on his tongue, but had gone by that morning. Four days later the patient reported that the infection tried to come up all over but failed and he was all clear.

On Apr. 4, 1984 the patient reported with a lesion on his chin which had developed the previous day. He also reported a nocturnal headache the previous night. He stated that these were the first problems he had had since his treatment on Feb. 9, 1984. He was administered a further 4.75 cc TEA Cl solution (5.5 mg/kg body weight).

On July 10, 1984 the patient reported that the lesion had cleared 3 days after the infusion and that he had had no further lesions until one developed in the preceding week. He reported that he had had no further nocturnal headaches.

CLINICAL CASE J

Patient J is a 50 year old female who weighed 66 kg when she reported for treatment on Jan. 26, 1984. She was diagnosed as having HSV Type 2. She described a history of sacral lesions during the past 4 years which occurred every 2-3 months. Lesions lasted for 5-30 days. On Jan. 26, 1984, she reported moderate pain, itching and stinging in the sacral region commencing the previous night.

She was infused with 3.6 cc. of TEA Cl(5.5 mg/kg) and experienced some blurred vision immediately following the treatment.

On Jan. 28, 1984 the patient reported that the pain had disappeared and that the lesions were drying. Five days later the patient reported that blisters had appeared two days previously but had now cleared. On Mar. 31, 1984 the patient reported tingling blisters and on May 1, 1984 she was given TEA Cl in a 1% concentration in a hydrophilic ointment base for topical administration. The following day she reported that the tingling and redness had gone but that 2 more vesicles had appeared. Three days later the patient reported that all the lesions had dried up.

The patient was again contacted on July 10, 1984 when she reported that she had since had one attack (commencing on approximately June 18, 1984) but that the lesions had only lasted 3 days. On that occasion the patient had once again applied the ointment. Since then she has had no further attacks.

CLINICAL CASE K

Patient K is a 34 year old female who weighed 59 kg. when she reported for treatment on Apr. 4, 1984. She was diagnosed as having HSV Type 2 since October 1977. She described a history of lesions on the buttocks and genital region with attacks occurring monthly in cooler weather and weekly in warmer weather. She said her last attack had occurred one week prior to her reporting for treatment. The patient was infused with 3.1 cc. on Apr. 4, 1984 after which she experienced some blurred vision. On Apr. 27, 1984 the patient reported that she felt a massive attack coming. On the same day the patient was administered a further 3.4 cc. of TEA Cl after which she once again experienced blurred vision. On July 12, 1984 the patient reported that that attack had not occurred. She said that she had since had 2 shorter attacks (of about 2-3 days each) both of which were of a milder severity.

CLINICAL CASE L

Patient L is a 49 year old female who weighed 53 kg. when she reported for treatment on May 9, 1984. She was referred by a Board Certified Dermatologist who had performed facial dermabrasion on her on May 3, 1984. She had developed HSV Type 1 lesions throughout the area of the surgery. After the development of the surgical complication, the patient could recall one previous lesion in a localized area some years previously.

The patient was infused with 2.9 cc. of TEA Cl (5.5 mg/kg) after which she experienced some blurred vision. On May 13, 1984 the patient reported that she had felt badly for 24-36 hours following the treatment but had since felt quite well.

On June 3, 1984 the patient's referring dermatologist advised that on the 7th day after the treatment, the crusting had all disappeared. He observed that in his experience this would normally have taken 3 weeks until DMSO was introduced, after which time he had still not seen it take less than 2 weeks.

CLINICAL CASE M

Patient M is a 22 year old female with a history of HSV Type 1 infections extending over a period of more than 2 years. When she reported for treatment on May 2, 1984, she described a history of labialis lesions occurring every 2-3 months and lasting approximately 14 days. The lesions would typically begin as blisters then spread out to a more extensive area. When the patient reported on May 2, 1984 a lesion had begun 2½ days previously. She was given an ointment containing a 1% concentration of TEA Cl in a hydrophilic ointment base for topical administration. On May 7, 1984 the patient reported that the lesions had cleared.

On July 8, 1984 the patient once again reported that a labialis lesion had developed and that she had once again resumed administration of the ointment. On July 11, 1984 the patient reported that the lesion had not spread and had now crusted.

Conclusions From In Vitro Experiments And Clinical Testing

From the above clinical cases, it is clearly seen that administration of TEA is effective in alleviating HSV Types 1 and 2 symptoms. The degree of relief and the duration of the relief varies from patient to patient, ranging from a minor short-term effect to complete remission of the disease. In some cases no improvement has been reported. Thus, while treatment with TEA is not the answer to all HSV problems, it can provide very significant and welcome relief for those patients that do respond. As more experience with TEA treatment is accumulated, it can be expected that its benefits can be maximized.

Applicant is not bound to any theory relating to the mechanism of TEA effectiveness.

Because many varying and different embodiments may be made within the scope of the inventive concept herein taught, and because many modifications may be made in the embodiments herein detailed in accordance with the descriptive requirements of the law, it is to be understood that the details herein are to be interpreted as illustrative and not in a limiting sense.

What is claimed is:

1. A method for treating infection in a mammal caused by Herpes Simplex Virus Type 2 comprising the step of vaginally administering to said mammal TEA halide in an effective dosage to treat infection in a mammal caused by Herpes Simplex Virus Type 2.

2. The method of claim 1, wherein the treatment reduces the shedding of the Herpes Simplex Virus Type 2 by a mammal infected by the virus.

3. The method of claim 1, wherein the treatment reduces the frequency of the recurrence of symptoms of a disease in a mammal caused by Herpes Simplex Virus Type 2.

4. The method of claim 1, wherein the treatment reduces the duration of symptoms of a disease in a mammal caused by Herpes Simplex Virus Type 2.

5. The method of claim 1, wherein the treatment reduces the severity of symptoms of a disease in a mammal caused by Herpes Simplex Virus Type 2.

6. The method of claim 1, wherein the TEA halide is administered in a pharmaceutically acceptable diluent in an amount within the range of about 0.1% to about 50% by weight.

7. A method for treating infection in a mammal caused by Herpes Simplex Virus Type 1 comprising the step of vaginally administering to said mammal TEA halide in an effective dosage to treat infection in a mammal caused by Herpes Simplex Virus Type 1.

8. A method of claim 7, wherein the treatment prevents or reduces the shedding of Herpes Simplex Virus Type 1 by a mammal infected by said virus.

9. The method of claim 7, wherein the treatment reduces the frequency of the recurrence of symptoms of a disease in a mammal caused by Herpes Simplex Virus Type 1.

10. The method of claim 7, wherein the treatment reduces the duration of symptoms of a disease in a mammal caused by Herpes Simplex Virus Type 1.

11. The method of claim 7, wherein the treatment reduces the severity of symptoms of a disease in a mammal caused by Herpes Simplex Virus Type 1.

12. The method of claim 7, wherein the TEA halide is administered in a pharmaceutically acceptable diluent in an amount within the range of about 0.1% to about 50% by weight.

* * * * *